US010013769B2

(12) United States Patent
Gärber

(10) Patent No.: US 10,013,769 B2
(45) Date of Patent: Jul. 3, 2018

(54) DEVICE FOR PROCESSING TOMOGRAPHIC DATA FOR VISUALIZING THE COURSE OF A THERAPY

(71) Applicant: Drägerwerk AG & Co. KGaA, Lübeck (DE)

(72) Inventor: Yvo Gärber, Breitenfelde (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 172 days.

(21) Appl. No.: 14/962,463

(22) Filed: Dec. 8, 2015

(65) Prior Publication Data

US 2016/0163062 A1 Jun. 9, 2016

(51) Int. Cl.

| | |
|---|---|
| ***G06K 9/00*** | (2006.01) |
| ***G06T 7/00*** | (2017.01) |
| ***A61B 5/053*** | (2006.01) |
| ***A61B 6/03*** | (2006.01) |
| ***A61B 8/00*** | (2006.01) |
| ***G06T 7/62*** | (2017.01) |
| *A61B 5/055* | (2006.01) |

(52) U.S. Cl.

CPC .......... *G06T 7/0085* (2013.01); *A61B 5/0536* (2013.01); *A61B 6/032* (2013.01); *A61B 8/00* (2013.01); *G06T 7/0016* (2013.01); *G06T 7/62* (2017.01); *A61B 5/055* (2013.01); *G06T 2207/10072* (2013.01); *G06T 2207/10081* (2013.01); *G06T 2207/10088* (2013.01); *G06T 2207/30061* (2013.01); *G06T 2207/30076* (2013.01)

(58) Field of Classification Search

None

See application file for complete search history.

(56) References Cited

U.S. PATENT DOCUMENTS

| | | | |
|---|---|---|---|
| 4,075,482 | A | 2/1978 | Périlhou |
| 4,149,081 | A | 4/1979 | Seppi |
| 4,806,867 | A | 2/1989 | Hanawa et al. |
| 5,807,251 | A | 9/1998 | Wang et al. |

(Continued)

FOREIGN PATENT DOCUMENTS

| | | | |
|---|---|---|---|
| CN | 101564294 | A | 10/2009 |
| CN | 102755163 | A | 10/2012 |
| CN | 102821684 | A | 12/2012 |

OTHER PUBLICATIONS

Gomez-Laberge, Camille, John H. Arnold, and Gerhard K. Wolf. "A unified approach for EIT imaging of regional overdistension and atelectasis in acute lung injury." IEEE transactions on medical imaging 31.3 (2012): 834-842.*

(Continued)

*Primary Examiner* — Nirav G Patel

(74) *Attorney, Agent, or Firm* — McGlew and Tuttle, P.C.

(57) ABSTRACT

A device (10) for processing data (3), which were obtained from a medical device suitable for imaging the lungs or the thorax, particularly an electrical impedance tomography device (30), provides improved visualization of a three-dimensional thoracic dimension (350) of the lungs. A characteristic contour (34, 350) is determined continuously by continuous reference to a previously determined outer contour (905) of the lungs as a comparison variable and is outputted, provided and visualized as an output signal (35).

20 Claims, 1 Drawing Sheet

(56) References Cited

U.S. PATENT DOCUMENTS

| | | | |
|---|---|---|---|
| 6,236,886 | B1 | 5/2001 | Cherepenin et al. |
| 6,944,330 | B2 | 9/2005 | Novak et al. |
| 7,717,849 | B2 | 5/2010 | Mathew et al. |
| 8,170,640 | B2 | 5/2012 | Kiraly et al. |
| 2009/0118634 | A1 | 5/2009 | Weiler |
| 2011/0061650 | A1 | 3/2011 | Heesch |

OTHER PUBLICATIONS

Heizmann et al.: "3-D Lung Visualization Using Electrical Impedance Tomography Combined with Body Plethysmography", Institute of Technical Medicine, Furtwangen University, Villingen-Schwenningen, Germany, publication date 2014, pp. 172-175.
Ferrario et al.: "Toward Morphological Thoracic EIT: Major Signal Sources Correspond to Respective Organ Locations in CT", IEEE Transactions on Biomedical Engineering, vol. 59, No. 11, Nov. 2012, pp. 3000-3008.
Swisstom $BB^2$ Produktinformationen: Sehen Sie die Lunge atmen!, EIT-Monitoring in Echtzeit. Tomografische Bilder in Echtzeit zur Überwachtung von Organfunktionen and zur Diagnostik. Swisstom AG, Schulstrasse 1, CH 7302, Landquart, Schweiz, www.swisstom.com.

* cited by examiner

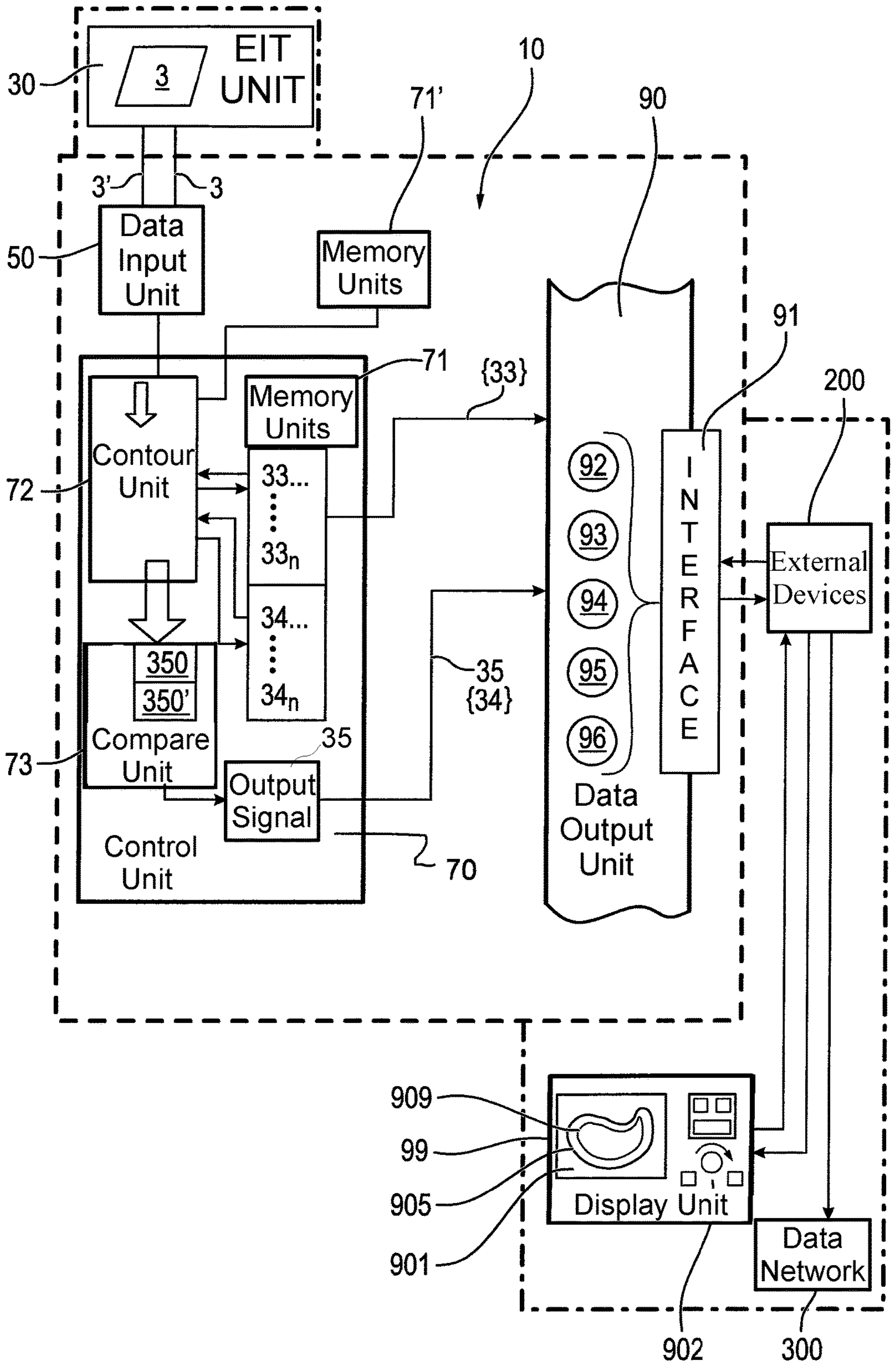
EIT UNIT
3
30
3'
3
10
71'
90
Data Input Unit
50
Memory Units
Memory Units
71
{33}
Contour Unit
72
33...
$33_n$
34...
$34_n$
350
350'
Compare Unit
73
35
Output Signal
35
{34}
Control Unit
70
92
93
94
95
96
INTERFACE
91
Data Output Unit
200
External Devices
909
99
905
901
Display Unit
902
Data Network
300

DEVICE FOR PROCESSING TOMOGRAPHIC DATA FOR VISUALIZING THE COURSE OF A THERAPY

CROSS REFERENCE TO RELATED APPLICATIONS

This application claims the benefit of priority under 35 U.S.C. § 119 of German Patent Application 10 2014 018107.3 filed Dec. 9, 2014, the entire contents of which are incorporated herein by reference.

FIELD OF THE INVENTION

The present invention pertains to a device for processing and visualizing data relating to a three-dimensional thoracic dimension of the lungs, wherein the data were obtained from a medical device suitable for generating data for imaging, especially from an electrical impedance tomography device. The three-dimensional thoracic dimension of the lungs corresponds to a position and extension of the lungs of a patient within the patient's thorax.

BACKGROUND OF THE INVENTION

Devices for electrical impedance tomography (EIT) are known from the state of the art. These devices are designed and intended for generating an image, a plurality of images or a continuous sequence of images from signals obtained by means of electrical impedance measurements and data and data streams obtained therefrom. These images or sequences of images show differences in the conductivity of different tissues of the body, bones, skin, body fluids and organs, especially the lungs, which are useful for observing the situation of a patient.

U.S. Pat. No. 6,236,886 describes an electrical impedance tomograph with an array of a plurality of electrodes, power input at at least two electrodes and a method with an algorithm for image reconstruction for determining the distribution of conductivities of a body, such as bone, skin and blood vessels in a general embodiment with components for signal detection (electrodes), signal processing (amplifier, A/D converter), power input (generator, voltage/current converter, current limitation) and with components for controlling (C).

It is stated in U.S. Pat. No. 5,807,251 that it is known in the clinical application of EIT that a set of electrodes is provided, which are arranged at a defined distance from one another, for example, around the chest of a patient in electrical contact with the skin. An electric current or voltage input signal is to be applied alternatingly between different pairs of electrodes or between all the possible pairs of electrodes among electrodes arranged mutually adjacent to one another. While the input signal is applied to one of the pairs of electrodes arranged mutually adjacent to one another, the currents or voltages are measured between each pair of the other electrodes, which pairs are located adjacent to one another, and the measured data obtained are processed in the known manner in order to obtain a visualization of the distribution of the specific electric resistance over a cross section of the patient, around which the electrode ring is arranged, and to display it on a display screen.

In addition to devices for electrical impedance tomography (EIT), further medical devices suitable for imaging, for example, a great variety of radiological devices, such as X-ray apparatuses (X-ray), computed tomographs (CTs), nuclear magnetic resonance (NMR) devices, nuclear spin or magnetic resonance tomographs (MRI), as well as also sonographic devices for imaging, which make possible imaging and the providing of signals or data, as well as devices for so-called bioimpedance measurement or impedance plethysmography, are used in the area of health care. Thus, an X-ray tomography system based on gamma radiation is known from U.S. Pat. No. 4,075,482 A. U.S. Pat. No. 4,806,867 A shows a magnetic resonance imaging system. A device for improved image reconstruction of computed tomograms is described in U.S. Pat. No. 4,149,081 A. A computer-assisted system for pulmonary diagnostics, which makes it possible to identity anatomic structures of volumetric medical images, is known from U.S. Pat. No. 6,944,330 B2. A sonography device, which is suitable for an examination of the lungs and for the diagnosis especially of pulmonary diseases, especially pulmonary embolism, is known from U.S. Pat. No. 8,170,640 BB. U.S. Pat. No. 7,717,849 B2 describes a method and a device for controlling a display device in an ultrasound device, wherein selected elements of a dimensional visualization are transformed into another dimensional visualization.

Unlike imaging methods using X-ray or gamma radiation, electrical impedance tomography (EIT) has the advantage that no radiation burden that is disadvantageous for the patient occurs. Unlike sonographic methods, EIT makes possible image acquisition over a representative cross section of the entire thorax and the lungs of the patient by means of the electrode belt. In addition, the need for using a contact gel, which must be applied before each examination and thus makes a continuous sonographic examination over a longer period of time difficult, is eliminated. Thus, electrical impedance tomography (EIT) offers the advantage of making a continuous monitoring of the lungs possible in order to observe and document the course of a therapy of an artificially ventilated or spontaneously breathing patient.

It is possible by means of electrical impedance tomography (EIT) to generate so-called EIT image data for a two-dimensional image of the lungs in the plane in which the EIT electrodes are placed horizontally through the thorax of a patient. Due to the position of the EIT electrodes around the thorax, it is not possible therefore to generate frontal views or lateral views, but images are generated in the horizontal plane, the so-called transverse plane, in the EIT electrodes placed around the thorax. Additional image data can be generated for a nearly three-dimensional image of the lungs and additional views can be subsequently generated by computing in the plane of the body, such as a frontal view or sagittal view, by placing additional EIT electrodes around the thorax in different horizontal positions.

The regional distribution of the breathing air in the lungs of a patient can be considered by means of the EIT image data of electrical impedance tomography (EIT). The availability of an individually available thoracic dimension of the lungs within the individual thorax of the patient in question is of great advantage for the assessment of the current status of an artificially ventilated or spontaneously breathing patient.

SUMMARY OF THE INVENTION

An object of the present invention is to provide a device for processing tomographic data in order to visualize the course of a therapy.

Another object of the present invention is to provide a device that makes it possible to continuously determine and provide a current thoracic dimension of the lungs of a patient.

According to the invention a device is provided for processing and visualizing data of at least one area of the lungs and of the thorax for determining and visualizing a three-dimensional thoracic dimension of the lungs over an observation period. The device comprises a data input unit for receiving data obtained from a medical device, suitable for imaging the lungs or the thorax, the data input unit being configured to receive and provide the data of at least one area of the lungs or of the thorax a computing and control unit and a data output unit. The computing and control unit is configured to determine a first image data set which represents a first characteristic outer contour of the lungs, from data for a first ventilation situation and to generate and provide an output signal which represents the first characteristic outer contour of the lungs and to determine at least one additional image data set, which additional image data set represents an additional characteristic outer contour of the lungs, from data for at least one additional ventilation situation. The computing and control unit compares the first image data set with the at least one additional image data set on the basis of a comparison criterion and generates and provides the output signal, as a function of the comparison, on the basis of the first image data set or on the basis of the second image data set. The data output unit is configured to output, provide or represent the characteristic outer contour of the lungs corresponding to the output signal.

Some of the terms used within the framework of this patent application will be explained in more detail as follows.

A time segment in a time course is defined as the observation period in the sense of the present invention. The beginning and the end of such an observation period are defined either by fixed or adaptable times or by events, which are determined by breathing or ventilation. Examples of observation periods, which are based on breathing or ventilation, are a breathing cycle, a plurality of breathing cycles, parts of breathing cycles, such as breathing in (inspiration), inspiratory pause, breathing out (expiration), expiratory pause, as well as also parts of one or more breathing cycles, e.g., a plurality of inspirations, a plurality of expirations. Further observation periods, especially in case of artificial ventilation, may be time periods with defined pressure levels, such as plateau pressure PIP, PIP pressure (Positive Inspiratory Pressure, PIP), or PEEP pressure (Positive End Expiratory Pressure, PEEP), PIP or PEEP pressure stages, rising or declining PIP pressure ramps or PEEP pressure ramp as part of a special ventilation maneuver or time segments, which correspond to defined properties of ventilation modes (e.g., Bi-Level Positive Airway Pressure, BiPAP).

Tomographic data are defined in the sense of the present invention as the following signals or data:

- raw EIT data, i.e., measured signals detected with an EIT device by means of a group of electrodes or by means of an electrode belt, such as voltages or currents, associated with electrodes or groups of electrodes or with positions of electrodes or of groups of electrodes on the electrode belt;
- EIT image data, i.e., data or signals that are determined from the raw EIT data and represent local impedances, impedance differences or impedance changes of areas of the lungs of a patient;
- data of a medical device, which provides an imaging based on computed tomography (CT) or X-ray radiation (X-ray);
- data of a medical device, which provides imaging based on magnetic resonance imaging (MRI) or on nuclear spin tomography, data of a medical device that provides imaging based on sonography (ultrasound), or data of a medical device that provides imaging based on bioimpedance measurement or plethysmography.

For processing and visualizing data for at least one area of the lungs or thorax, which data were obtained by means of a medical device suitable for generating data for imaging, especially of an electrical impedance tomography device, the device according to the present invention comprises:

- a data input unit,
- a computing and control unit; and
- a data output unit.

The data input unit is configured to receive and provide data of at least one area of the lungs or of the thorax. The data represent, for a plurality of lung areas, regional ventilation situations of the lungs for at least one location of the lungs over an observation period. The data input unit preferably has interface elements for this, for example, level converters, amplifiers, A/D converters, components for overvoltage protection, logic elements and additional electronic components for the wired or wireless reception of the data and signals, as well as adaptation elements such as code or protocol conversion elements for adapting the signals and data for the further processing in the computing and control unit.

The computing and control unit is configured to determine a first image data set, which represents a first characteristic outer contour of the lungs, from the data for a first ventilation situation, and to generate and provide an output signal, which represents the first characteristic outer contour of the lungs.

The computing and control unit is configured, furthermore, to determine at least one additional image data set, which represents an additional characteristic outer contour of the lungs, from the data for at least one additional ventilation situation.

The computing and control unit is configured, furthermore, to compare the first image data set with the at least one additional image data set on the basis of a comparison criterion and to generate and provide the output signal as a function of the comparison on the basis of the first image data set or on the basis of the second image data set. The computing and control unit has elements for data processing, computing and process control, such as microcontrollers (μC), microprocessors (μP), digital signal processors (DSP), logical units—Field-Programmable Gate Array (FPGA), Programmable Logic Device (PLD), memory components—Read-Only Memory (ROM), Random Access Memory (RAM), Synchronous Dynamic Random Access Memory (SD-RAM) and combination variants thereof, for example, in the form of an "embedded system," which are designed together with one another and are adapted to one another and are configured by programming to carry out the necessary steps for processing and visualizing data obtained by means of a medical device suitable for degenerating data for imaging for a three-dimensional thoracic dimension of the lungs within the thorax of a patient during the observation period. The image data sets contain contour information on the three-dimensional thoracic dimension of the lungs in the thorax. The three-dimensional thoracic dimension of the lungs in the thorax is determined, on the one hand, by the position of the lungs in relation to the vertical body axes (sagittal body plane and frontal body plane) and the horizontal body axis (transverse body plane) and, on the other hand, by the distance of the lungs from ribs, sternum (retrosternally) and spine (prevertebrally). The circumference of the thorax thus determines essentially the maximum thoracic dimension, which the lungs can assume in the thorax. The thoracic dimension of the lungs comprises, in this case, the shape, form, extension, circumference or even areas projected to the body axes, as they are usual for visualization in medical imaging. In principle, especially the transverse view is employed for electrical impedance tomography (EIT). Especially the outer contour of the lungs of the patient is obtained as a three-dimensional thoracic dimension in this transverse view of the electrical impedance tomography (EIT) as a projection in the horizontal plane in the horizontal position of the EIT electrodes placed around the patient's thorax.

It is therefore essential for the present invention that contour information is obtained from the tomographic data provided as image data sets for output and display of the three-dimensional thoracic dimension of the lungs, especially of the characteristic outer contour. The image data sets are determined continuously at different times from the tomographic data in order to determine and provide a particular current outer contour. The particular current outer contour is compared to the characteristic outer contour being displayed on the basis of a specific comparison criterion, which can preferably be selected or set by the user. Finally, the previous outer contour continues to be outputted as a characteristic outer contour depending on the result of the comparison and/or the display is left unchanged or replaced with the output and/or visualization of the outer contour last detected. The particular outer contour of the lungs, which was outputted and/or displayed last, will hereinafter be used as and called a characteristic outer contour of the lungs. The size of the circumference of the lungs and/or the size of the lung area projected in the body plane and/or special shapes of outer contours of the lungs will preferably be used as a specific comparison criterion.

Examples and samples of special shapes of outer contours of the lungs can be derived, for example, on the basis of typical circumferential shapes or typical area shapes of lung images from the tomographic imaging of the lungs.

It is decisive for the continuous determination and provision of a current three-dimensional thoracic dimension of the lungs of a patient as well as for visualizing same and for making it possible to use and analyze same for the therapeutic result that the visualized three-dimensional thoracic dimension of the lungs of the patient be in relation to the current health status of the patient. The device according to the present invention offers the user the possibility of placing the current tomographic data in a context to the characteristic outer contour of the lungs of the patient. If, for example, the computing and control unit preferably uses a maximum outer contour as a characteristic outer contour of the lungs of the patient by means of a comparison of the circumference or area of the lungs, the user is thus enabled to put the current tomographic data or image data in relation to a situation of the lungs with maximum ventilation. This makes it possible for the user, for example, if the current ventilated contour of the lungs is small compared to the previously determined maximum outer contour, to take this as an indicator that the ventilation can still be optimized for this patient. Such an optimization can then be carried out without undue delay by changing or adapting ventilation parameters, for example, the respiration rate, the inspiration-to-expiration ratio (I:E ratio), inspiratory and expiratory pause times, ventilation pressures (PEEP pressure, PIP pressure) or even by changing the dosage of certain drugs. In addition, the continuous determination and provision of the current three-dimensional thoracic dimension (maximum outer contour) of the lungs of the patient also offers the possibility of selecting a further and, for example, larger and hence improved new maximum outer contour as a new valid characteristic outer contour due to the recovery or due to the change in ventilation parameters and of continuously and automatically resetting, as it were, the reference point, to which the user can then adapt the subsequent further tomographic data and image data.

For processing the tomographic data and for performing the comparison of the outer contours therefor, the computing and control unit is configured to suitably select and apply a method from a group of mathematical methods for signal and data analysis, such as

- mathematical model functions for data separation, such as Principal Component Analysis; PCA), Independent Component Analysis; ICA),
- mathematical methods for image processing, such as pixel mapping,
- mathematical methods for data comparison, such as correlation functions,
- statistical methods for data comparison, such as computations, analyses and sorting of data sets based on distribution functions, frequency distributions, standard deviation, scattering, mean value or median,
- transformations, such as Discrete Fourier Transform (DFT), Fast Fourier Transform (FFT), Z Transform, LaPlace Transform, wavelet transform, in order to determine the characteristic outer contour as a three-dimensional thoracic dimension of the lungs from the tomographic data.

The data output unit is configured to output, provide or visualize the characteristic outer contour of the lungs with the use of the output signal.

The data output unit is configured to generate, provide or visualize the output signal. The output signal is preferably configured as a video signal (e.g., Video Out, Component Video, S-Video, HDMI, VGA, DVI, RGB) to make possible a graphic, numeric or pictorial visualization of a three-dimensional thoracic dimension of the lungs within the thorax of a patient during the observation period on a display unit connected to the output unit in a wireless or wired manner (WLAN, Bluetooth, WiFi) or on the data output unit itself.

In a preferred embodiment, the comparison criterion is based on a difference in the size, in the circumference or in the size in the area of the first characteristic outer contour of the lungs and the additional characteristic outer contour of the lungs.

In another preferred embodiment, a maximum outer contour of the lungs within the thorax is determined as the characteristic outer contour of the lungs based on the circumference and/or on the area of the characteristic outer contour of the lungs.

In another preferred embodiment, the characteristic outer contour of the lungs is determined relative to a predefined time interval or an observation period.

In a special embodiment variant, boundary conditions of the EIT acquisition are also included in the determination of the characteristic outer contour.

Information on the diameter of an electrode belt, which was used to obtain EIT data, may be included as a boundary condition of the EIT acquisition in order to ensure the plausibility of the characteristic outer contour in respect to the circumference of the patient's thorax.

Anatomic boundary conditions are also included in the determination of the characteristic outer contour in a special embodiment variant in order to check the plausibility of the characteristic outer contour determined. Anatomic boundary conditions may be derived, for example, from information on age, height, body weight and gender of the patient. For example, the circumference of the patient's thorax can be approximately estimated in many cases from gender, height and body weight.

A number of previous maximum outer contours of the lungs within a predetermined time interval or an observation period is also included in the determination of the characteristic outer contour in another embodiment.

In another embodiment, the determination of the characteristic outer contour is performed by means of filtering the data or image data sets over a predetermined time interval or an observation period in order to achieve an improvement of the characteristic outer contour. Many different types of signal smoothing, such as frequency filtering, averaging or median filtering may be preferably used.

A comparison with a predetermined, anatomically typical, stored comparison shape is performed for determining the characteristic contour in a special embodiment variant. The anatomically typical comparison shape is preferably stored in the form of a transverse visualization of the lungs and may have preferably been obtained by means of an electrical impedance tomography device, but also by means of other devices suitable for medical imaging (CT, MRI, sonography, X-ray, plethysmography). This makes it possible to compensate possible defects in the contour or in the course of the contour and thus to obtain a closed characteristic outer contour and to improve the shape of the contour.

In a preferred embodiment, the data of the medical device suitable for imaging are provided as data of an electrical impedance tomography device. The data represent local impedance values of the lungs or of the thorax in different ventilation situations of the lungs.

In a preferred embodiment, the data input unit, the computing and control unit or the data output unit are configured as components of the electrical impedance tomography device, or the data input unit, the computing and control unit or the data output unit are combined with the electrical impedance tomography device into a medical system.

In another preferred embodiment, the data of the medical device suitable for imaging are provided as data of an electrical impedance tomography measuring unit, of a computed tomography device (CT), of a nuclear spin tomography or magnetic resonance imaging (MRI) device, of a bioimpedance measuring device, of an impedance plethysmography device or of a sonographic medical device.

The embodiments described represent, in themselves as well as combined with one another, special embodiments of the device according to the present invention for processing and visualizing data obtained by means of a medical device suitable for generating data for imaging in respect to a three-dimensional thoracic dimension of the lungs within the thorax of a patient. Advantages arising from a combination or combinations of a plurality of embodiments and further embodiments are equally covered by the idea of the invention, even though not all possibilities of combination of embodiments are described in detail for this.

The present invention will be explained now in more detail by means of the following figures and the corresponding description of the figures without limitations of the general idea of the invention. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view of functional elements for processing EIT data.

DESCRIPTION OF THE PREFERRED EMBODIMENTS

Referring to the drawings, FIG. 1 shows a device 10 composed of functional elements for processing EIT data 3 in a schematic form.

This device 10 comprises as the basic components a data input unit 50, a computing and control unit 70 and a data output unit 90. The connections between the elements and units of the device 10 are shown only schematically in this embodiment according to this FIG. 1; for example, the essential data connections and data inputs and data outputs are shown, but no supply lines are shown, and not all connection lines between the elements and units with one another are shown. Furthermore, a display unit 99 connected to the data output unit 90 is shown in this FIG. 1. The display unit 99 comprises visualization means 901, such as display elements, display screens, displays for visualizing graphics, curves, diagrams or images or even numerical value displays for reproducing numerical values. Furthermore, the display unit 99 comprises input elements and operating elements 902, such as switches, buttons, knobs, and rotary knobs.

A special embodiment variant is a touch-sensitive display (touch screen) with combination of input and visualization functionalities.

The data input unit 50 inputs EIT data 3 from an EIT device 30. In this embodiment shown in FIG. 1, the EIT device 30 is connected as an external measuring unit to the device 10 with an electrode array, not shown in this FIG. 1. However, optional technical variants of the embodiment according to this FIG. 1 are may be provided according to the invention, wherein the EIT device 30 may be configured as a component of the device 10, and the device 10 may also be configured as a part of the EIT device 30. The display unit 99 is configured in this embodiment shown in FIG. 1 as an external device connected to the device 10 composed of elements, but the device 10 may also be made together with the display unit 99 to form a global EIT system in an optional technical variant in the sense of the present invention. A detailed representation of these optional technical embodiment variants is not shown in FIG. 1 for reasons of clarity, and the integration of the device 10 composed of functional elements with the EIT device 30 and/or with the display unit 99 is indicated only by dots, dashes and lines in the view shown in FIG. 1. The data input unit 50 stores the data after inputting for further processing either in an unchanged format as EIT data 3 or in a form adapted for a further processing as preprocessed EIT image date 3'. The data output unit 90 is configured to provide data or signals, for example, an output signal 35 from the computing and control unit 70 at an interface 91 for a visualization as numbers 92, images 93, diagrams 94, signal curves or curves over time 95 or compilations 96 of data on a display unit 99 (display screen, monitor, data display unit). Provision is defined in the sense of the present invention as any form of providing a signal or data for transmission, outputting, visualization, display, printing, sending, further processing to additional devices or to parts of devices. The display unit 99 is configured in this FIG. 1 as an external device connected to the data output unit 90 via the interface 91. However, the scope of the present invention also covers the possibility of designing the display unit 99 as an external unit of the data output unit 90 or also of the device 10. For example, wireless or wired provision of data for a data network 300 (LAN, WLAN, Ethernet), wireless or wired provision of data for mutual transmission of measured values and control data (e.g., USB, RS232, RS485, FireWire, NMEA 0183, IrDA, Bluetooth, CAN, UMTS [SMS, MMS]) in data exchange with different other external devices 200 (anesthesia devices or ventilators, physiological monitors, monitors suitable for monitoring the cardiac minute volume, personal computers, hospital management systems), as well as the provision of audio/video data (e.g., Video Out, Component Video, S-Video, HDMI, VGA, DVI, RGB) in different data formats (e.g., MPEG, JPEG, etc.) for connection to the display unit 99 or to other display devices (display screens, monitors, tablet PCs) are possible by means of the interface 91. The computing and control unit 70 performs a plurality of tasks within the device 10, such as the coordination with the data input unit 50 and with the data output unit 90. The computing and control unit 70 is preferably configured, for example, as a central computing unit (CPU), a microprocessor (μP) or as an array of individual microcontrollers (μC).

The computing and control unit 70 comprises, furthermore, an internal memory unit 71 or is connected to an external memory unit 71'. The memory units 71, 71' are configured for storing and providing the EIT data 3, 3 as a set of data sets in the form of EIT image data sets {33}, {34}. The EIT data 3 or EIT image data 3' being stored by the data input unit 50 are stored and provided as image data sets 33, 33', 33", 33'", . . . **33*n* in the memory units 71, 71'. The computing and control unit 70 comprises a contour determination unit 72, which is configured to determine a set of contour data sets {34, 34', 34", 34'", . . . 34*n*}∈{34} from each of the image data sets from the set of image data sets {33, 33', 33", 33'", . . . 33*n*}∈{33} and to make it available to the memory units 71, 71' for storage. The contour data sets 34 contain information on the contour of the circumference and/or the area shape of the lungs within the thorax of a patient, not shown in this FIG. 1, especially relative to the transverse axis of the lungs. It is advantageous in this connection to perform a reduction of the image data sets during the generation of the contour data sets 34. For example, image data, which represent information on the center of the left or right lobe of the lung, may be stored in the contour data sets at the time of such a reduction with a lower information density than image data that contain information in the transition area of the lungs to surrounding body areas (ribs, diaphragm, myocardium, aorta, intercostal muscles). This leads, on the one hand, to a reduction in the amount of storage space needed in the memory unit 71, 71', and it becomes, in addition, possible to increase the speed at which the contour data sets 34 are processed due to the reduction, while a high acquisition rate is maintained. This is the prerequisite for the output, provision or visualization of the contour data sets in real time, i.e., with only a time delay between data generation and visualization in further steps of the data processing. Furthermore, a comparison unit 73, which is configured to perform a comparison of at least two contour data sets from the set of contour data sets 34', 34", 34'", . . . 34*n* and to determine therefrom the output signal 35, which reflects a characteristic contour 350 of the lungs within the thorax as a three-dimensional thoracic dimension of the lungs over an observation period, is provided in the computing and control unit 70. The comparison unit 73 preferably uses a size comparison of the contours of the circumference and/or area shapes of the lungs, which are contained in the contour data sets 34, as a criterion. The comparison of at least two contour data sets 34, 34' by the comparison unit 73** takes place as follows:

If the currently determined contour in the circumference or area with the use of the criterion is larger than the characteristic contour 350 determined previously, the current contour is selected as the current characteristic contour 350, and the output signal 35 is determined on the basis of this newly selected characteristic contour 350. A variant of a characteristic contour 350 is, for example, a lung outer contour 350', which represents the maximum extension of the lungs in the thorax over a preceding predetermined time interval or observation period. In a special embodiment variant, boundary conditions or preset values are also included in the determination of the characteristic contour 350 in order to ensure the plausibility of the characteristic contour 350. For example, information on the diameter of the electrode belt, not shown in this FIG. 1, which diameter was used to obtain EIT data 3, EIT image data 3' or the image data sets 33, 33', 33", 33'", . . . **33*n*, or a comparison with an anatomically typical comparison shape can be taken into account when determining the characteristic contour 350 or the outer contour 350' of the lungs. The output signal 35 is made available by the comparison unit 73 to the data output unit 90 as a characteristic contour 350 or the outer contour 350'** of the lungs.

The characteristic contour 350 or the outer contour 350' of the lungs is displayed on the visualization means 901 of the display unit 99.

A current ventilation situation of the lungs is schematically shown in this FIG. 1, based on the set of image data sets {33, 33', 33", 33'", . . . **33*n*}, as a graphic element in a transverse view of the lungs on the display unit 99 as an area contour 909. The characteristic contour 350 of the lungs, based on the set of contour data sets {34, 34', 34", 34'", . . . 34*n*}, is schematically shown in this FIG. 1 as another, graphically visualized element in a transverse view of the lungs as an outer contour 905 of the lungs on the display unit 99. It is seen on the display unit 99 in this way in what relation the current ventilation situation 909 of the lungs is to the outer contour 905 of the lungs. It can be derived from this to what extent the possibilities of lung ventilation individually given for this patient or these lungs are exhausted by the current ventilation situation 909**.

The described functional units of the computing and control unit 70 may be designed as individual components of the computing and control unit 70, but the present invention also covers the case in which the computing and control unit 70 may be integrated in other partial modules and may be configured by programming to provide the functions of the memory units 71, contour determination unit 72 and comparison unit 73, with the same effect as described in connection with FIG. 1 in the same form or in a modified form of processing.

While specific embodiments of the invention have been shown and described in detail to illustrate the application of the principles of the invention, it will be understood that the invention may be embodied otherwise without departing from such principles.

| | |
|---|---|
| 3, 3' | EIT data |
| 10 | Device composed of functional elements |
| 30 | EIT device |
| 33 | Image data sets |
| 34 | Contour data sets |
| 35 | Output signal |

-continued

| | |
|---|---|
| 50 | Data input unit |
| 70 | Computing and control unit |
| 71, 71' | Memory unit |
| 72 | Contour determination unit |
| 73 | Comparison unit |
| 90 | Data output unit |
| 91 | Interface |
| 92 | Numerical values |
| 93 | Images |
| 94 | Diagrams |
| 95 | Curves, courses of curves, signal curves over time |
| 96 | Data sets, data compilations |
| 99 | Display unit |
| 200 | External devices |
| 300 | Data network |
| 350, 350' | Three-dimensional thoracic dimension, characteristic contour, outer contour |
| 901, 902 | Visualization means, input means |
| 905 | Outer contour |
| 909 | Area contour |

What is claimed is:

1. A device for determining a position and extension of lungs of a patient over an observation period, the device comprising:

a patient imaging device for imaging a cross section of a thorax of the patient and generating data suitable for imaging the lungs in the cross section;

a data input unit for receiving the data obtained from the patient imaging device, the data input unit being configured to receive and provide the data of at least one area of the lungs or of the thorax;

a computing and control unit configured:

to determine a first image data set which represents a first characteristic outer contour of the lungs, from data for a first ventilation situation and to generate and provide an output signal which represents the first characteristic outer contour of the lungs;

to determine at least one additional image data set, which additional image data set represents an additional characteristic outer contour of the lungs, from data for at least one additional ventilation situation;

to compare the first image data set with the at least one additional image data set on the basis of a comparison criterion and to generate and provide an output signal, as a function of the comparison, on the basis of the first image data set or on the basis of the second image data set, the comparison criterion being based on at least one of a difference in size of at least one of a circumference of the lungs, and a difference in area between the first characteristic outer contour of the lungs and the additional characteristic outer contour of the lungs; and a data output unit configured to output, provide or represent the characteristic outer contour of the lungs corresponding to the output signal.

2. A device in accordance with claim 1, wherein a maximum outer contour of the lungs within the thorax is determined on the basis of at least one of a circumference of the lungs and an area of one of the characteristic outer contours of the lungs.

3. A device in accordance with claim 1, wherein at least one of the characteristic outer contours of the lungs is determined relative to a predetermined time interval or an observation period.

4. A device in accordance with claim 1, wherein boundary conditions of an electrical impedance tomography (EIT) acquisition are also included in the determination of at least one of the characteristic outer contours of the lungs.

5. A device in accordance with claim 1, wherein anatomic boundary conditions of the patient are also included in the determination of at least one of the characteristic outer contours of the lungs.

6. A device in accordance with claim 1, wherein a number of preceding maximum outer contours of the lungs within a predetermined time interval or an observation period are also included in the determination of at least one of the characteristic outer contours of the lungs.

7. A device in accordance with claim 1, wherein the computing and control unit filters the data or data sets over a predetermined time interval or an observation period in the determination of at least one of the characteristic outer contours of the lungs to improve the contour shape of the characteristic outer contour.

8. A device in accordance with claim 1, wherein a comparison with a predetermined, anatomically typical, stored comparison shape is performed in the determination of at least one of the characteristic outer contours of the lungs to improve the contour shape of the characteristic outer contour.

9. A device in accordance with claim 1, wherein the data of the medical device suitable for imaging are provided as one of:

data of an electrical impedance tomography device (EIT), wherein the data of the electrical impedance tomography device (EIT) represent local impedance values of the lungs or of the thorax in different ventilation situations of the lungs;

data of an electrical impedance tomography measuring unit;

data of a computed tomography device;

data of a nuclear spin tomography or magnetic resonance imaging (MRI) device;

data of a sonographic medical device; and data of a bioimpedance or impedance plethymsmography device.

10. A device for determining a position and extension of lungs of a patient over an observation period, the device comprising:

a patient imaging device for imaging a cross section of a thorax of the patient and generating data suitable for imaging the lungs in the cross section;

a data input unit configured to receive the data from the patient imaging device and provide electrical impedance tomography device lung area data or thorax area data;

a computing and control unit configured:

to determine a first image data set which represents a first characteristic outer contour of the lungs, from data for a first ventilation situation;

to determine at least one additional image data set, which additional image data set represents an additional characteristic outer contour of the lungs, from data for at least one additional ventilation situation;

to compare the first image data set with the at least one additional image data set on the basis of a comparison criterion and to generate and provide an output signal which represents a characteristic outer contour of the lungs, as a function of the comparison, on the basis of the first image data set or on the basis of the second image data set;

to perform a comparison with a predetermined, anatomically typical, stored comparison shape in the determination of the characteristic outer contour to improve the contour shape of the characteristic outer contour; and a data output unit configured to output, provide or represent the characteristic outer contour of the lungs corresponding to the output signal.

11. A device in accordance with claim 10, wherein the comparison is based on a comparison criterion comprising of at least one of a difference between the first image data set and the at least one additional image data set relating to a size at least one of a circumference of the lungs, and difference between the first image data set and the at least one additional image data set relating to an area between the first characteristic outer contour of the lungs and the additional characteristic outer contour of the lungs.

12. A device in accordance with claim 10, wherein a maximum outer contour of the lungs within the thorax is determined on the basis of at least one of a circumference of the lungs and an area of the characteristic outer contour.

13. A device in accordance with claim 10, wherein the characteristic outer contour is determined relative to a predetermined time interval or an observation period.

14. A device in accordance with claim 10, wherein boundary conditions of an electrical impedance tomography acquisition are also included in the determination of the characteristic outer contour.

15. A device in accordance with claim 10, wherein anatomic boundary conditions of the patient are also included in the determination of the characteristic outer contour.

16. A device in accordance with claim 10, wherein a number of preceding maximum outer contours of the lungs within a predetermined time interval or an observation period are also included in the determination of the characteristic outer contour.

17. A device in accordance with claim 10, wherein the computing and control unit filters the data or data sets over a predetermined time interval or an observation period in the determination of the characteristic outer contour to improve the contour shape of the characteristic outer contour.

18. A device in accordance with claim 10, wherein the electrical impedance tomography device data of at least one area of the lungs or of the thorax represent local impedance values of the lungs or of the thorax in different ventilation situations of the lungs.

19. A device in accordance with claim 1, wherein:

the patient imaging device is an electrical impedance tomography device.

20. A device for determining a position and extension of lungs of a patient over an observation period, the device comprising:

a patient imaging device for imaging a cross section of a thorax of the patient and generating data suitable for imaging the lungs in the cross section;

a data input unit for receiving the data obtained from the patient imaging device, the data input unit being configured to receive and provide the data of at least one area of the lungs or of the thorax;

a computing and control unit configured:

to determine a first image data set which represents a first characteristic outer contour of the lungs, from data for a first ventilation situation and to generate and provide an output signal which represents the first characteristic outer contour of the lungs;

to determine at least one additional image data set, which additional image data set represents an additional characteristic outer contour of the lungs, from data for at least one additional ventilation situation;

to determine a maximum outer contour of the lungs within the thorax on a basis of at least one of a circumference of the lungs and an area of one of the characteristic outer contours of the lungs;

to compare the first image data set with the at least one additional image data set on the basis of a comparison criterion and to generate and provide an output signal, as a function of the comparison, on the basis of the first image data set or on the basis of the second image data set; and a data output unit configured to output, provide or represent the characteristic outer contour of the lungs corresponding to the output signal.

* * * * *

UNITED STATES PATENT AND TRADEMARK OFFICE

CERTIFICATE OF CORRECTION

PATENT NO. : 10,013,769 B2
APPLICATION NO. : 14/962463
DATED : July 3, 2018
INVENTOR(S) : Gärber It is certified that error appears in the above-identified patent and that said Letters Patent is hereby corrected as shown below:

On the Title Page

Please add item (30) Foreign Application Priority Data:
Dec. 9, 2014 (DE) ................................10 2014 018 107.3

Signed and Sealed this
Thirtieth Day of October, 2018

Andrei Iancu
*Director of the United States Patent and Trademark Office*